United States Patent [19]

Johst et al.

[11] 4,081,884
[45] Apr. 4, 1978

[54] METHOD FOR MAKING DIMENSIONALLY STABLE ARTICLES

[75] Inventors: Wolfgang Johst, Gevelsberg; Axel Friese, Wuppertal, both of Germany; Stefan Simon, Moedling, Austria

[73] Assignee: Dr. Carl Hahn, GmbH, Dusseldorf, Germany

[21] Appl. No.: 795,975

[22] Filed: May 11, 1977

[51] Int. Cl.² .................... D04H 1/22; A61F 13/20
[52] U.S. Cl. ........................................ 28/119; 100/38
[58] Field of Search ............... 19/144.5; 28/118, 119, 28/120; 100/38, 244, DIG. 5; 128/270, 285

[56] References Cited
U.S. PATENT DOCUMENTS 2,076,389   4/1937   Voss ........................................ 28/119
2,433,675   12/1947   Parish ................................ 28/118 X

*Primary Examiner*—Dorsey Newton
*Attorney, Agent, or Firm*—Jason Lipow

[57] ABSTRACT

A method is provided for manufacturing a dimensionally stable compressed article such as an absorbent catamenial tampon comprising compressed cellulosic fibers. The method comprises the steps of first radially compressing a cylindrical blank to form a radially compressed blank having a length in excess of the desired finished length; then axially compressing the blank in a heated chamber to a length less than the desired finished length; then allowing the blank to expand to the desired finished length; and then maintaining the blank at this length while still in the heated chamber until the blank obtains the desired stability.

10 Claims, 8 Drawing Figures

METHOD FOR MAKING DIMENSIONALLY STABLE ARTICLES

BACKGROUND OF THE INVENTION

This invention concerns a method for providing dimensionally stable absorbent bodies which comprise compressed cellulosic fibers. In particular, the invention concerns a method for compressing such bodies, in the form of cylindrical tampons, to insure against unwanted expansion after compression.

Absorbent, cylindrical tampons are now widely used for a number of absorbent purposes in the medical and dental field but are primarily used in the field of feminine hygiene as catamenial tampons. In this latter field, there are two basic types: digitally inserted tampons, inserted with the fingers, and applicator tampons, inserted with the aid of an applicator. Both types are usually made by folding or rolling a loosely associated, rectangular strip of absorbent material, usually fibrous and cellulosic in nature, into a blank and then compressing the blank into a cylindrically shaped product. In the case of digital tampons, the product is then wrapped and packaged and, in the case of applicator tampons, the product is first inserted into the applicator and then wrapped and packaged.

In both instances it is, of course, highly desirable that the tampon maintains its final compressed shape. Unfortunately, however, it has been found that after processing and even after packaging, the compressed absorbent material making up the tampon has a tendency to expand, first to a large degree just after compression and then to a lesser degree while being stored after packaging. This expansion, even when to a slight degree, results in a non-uniform sized product and is particularly bad in the case of applicator tampons where the applicator and tampon are each carefully sized to provide a balance between the force needed to expel the tampon in use and the frictional force needed to prevent the tampon from accidentally discharging from the applicator, both forces being functions of tampon size.

Accordingly, there is a need for a method of dimensionally stabilizing tampons.

SUMMARY OF THE INVENTION

There is provided, therefore, a method for manufacturing a relatively dimensionally stable absorbent body comprising compressed cellulosic fibers. The method comprises first radially compressing a generally cylindrical starting blank comprising cellulosic fibers, to form a radially compressed blank having a length which is in excess of the desired final length for the product. Preferably, the radially compressed blank is of a length of about 20 to about 40 percent in excess of the desired length for the finished tampon.

The radially compressed blank is then introduced into a heated chamber, preferably having wall temperatures of from about 120° C to about 150° C. It is advantageous to allow the blank to equilibrate in the chamber for a short period of time. Thereafter, the blank is axially compressed to a length less than the desired finished length (i.e. over-compressed), by continuously applying a force against at least one end of the blank while the remaining surfaces are held confined within the heated chamber. The force applied to the end of the blank should be applied gradually and continuously throughout the compression period.

Upon the blank attaining this over-compressed state, the force is released to an extent sufficient to allow the blank to recover and expand to the desired length of the finished product. Immediately upon the blank recovering to this desired length, further expansion is prevented by maintaining a resistant force against the end of the blank for a period of time while still maintaining the blank within the heated chamber. Thereafter, the blank is ejected from the chamber in essentially its finished form.

Quite surprisingly, a tampon blank undergoing this above-described over-compression process exhibits far different properties than compressed blanks of other known compression processes. Unlike prior compressed blanks, the products of this invention do not expand immediately to any noticeable degree and do not expand after staying for long periods of time in applicators or packaging. Additionally, it has been noted that the sidewalls of the cylindrical products made in accordance with this invention are advantageously smoother than other known products.

BRIEF DESCRIPTION OF THE DRAWINGS

FIG. 3a illustrates the injection step;
FIG. 3b illustrates the preheating step;
FIG. 3c illustrates the over-compressing step;
FIG. 3d illustrates the expansion and restraining steps; and
FIG. 3e illustrates the ejection step.

DETAILED DESCRIPTION OF THE INVENTION

Figure 1:
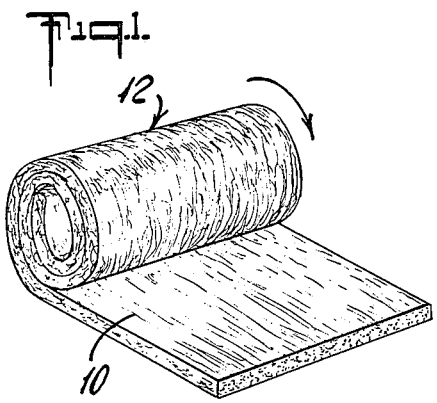
FIG. 1 schematically illustrates, in perspective view, one method of producing a blank for radial compression in accordance with the teachings of this invention.

Referring now to the drawings, illustrated therein is one specific embodiment for carrying out the teachings of this invention. Schematically illustrated in FIG. 1 is one method for preparing an uncompressed blank. A rectangular pad of absorbent material 10 is rolled into a spiral configuration to form a generally cylindrical blank 12. The pad 10 may comprise any of a number of absorbent materials or combinations thereof. Generally, however, such a pad comprises fibrous cellulosic materials and in particular cellulosic fibers of, for example, wood pulp, cotton or rayon. Such modified cellulosic materials as cellulosic ethers, e.g., carboxymethyl cellulose or the newly developed grafted cellulosic copolymers are also suitable. Also usable are non-cellulosic materials such as the hydrophilic synthetic polymers recently developed, e.g., hydrophilic polyurethane foams or even natural non-cellulosic materials such as hydrophilic starches. When the absorbent material is primarily fibrous, rectangular pads of these fibers will generally maintain sufficient integrity to be processed into blanks. Such pads will have, for example, a density ranging from about 0.06 to about 0.10 gm/cc. On the other hand where the materials are in powderous form, they may be combined with fibers to form a pad or may be held together by means of binders or the like. One possibility, for example, is to form a non-woven fabric from a combination of fibers and powders and use the fabric as an absorbent. It will be understood that a pad rolled into a spiral blank is not the only form that is satisfactory for a starting blank usable in connection with the teachings of this invention. For example, absorbent material can be enveloped by a generally cylindrically shaped sack of fluid pervious non-woven fabric and may be used in this form as well.

Figure 2A:
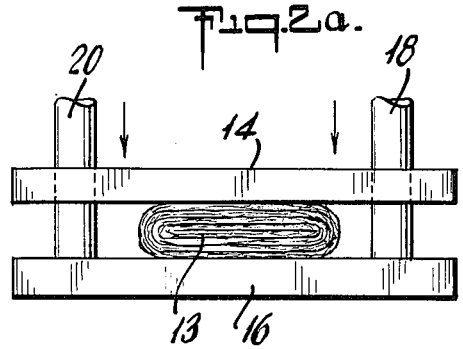
FIG. 2a schematically illustrates, in cross-sectional end view, a first step in one method of radially compressing the blank of FIG. 1 to produce a radially compressed blank for the method of this invention.
Figure 2B:
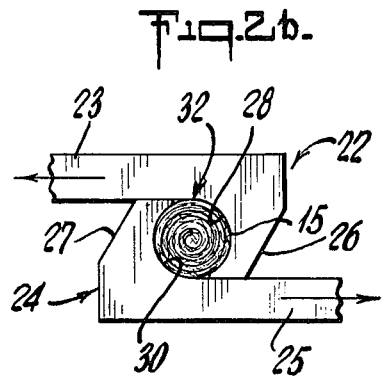
FIG. 2b schematically illustrates, in cross-sectional end view, a second step in the one method for radially compressing the blank of FIG. 1.

Irrespective of the materials of construction or the method for providing the blank, in accordance with the methods of this invention, the blank, having a length in excess of the desired final length, is first radially compressed. Several methods for radially compressing tampon blanks are known in the art. For example, in U.S. Pat. No. 3,845,520 issued on Nov. 5, 1974 to Stefan Simon, an apparatus and method is set out for performing such compression. Referring to FIG. 2a, the blank 12 is first compressed into a flattened cross-sectional shape by being inserted between two parallel shaping jaws 14, 16 which then move together compressing the blank therebetween. Preferably one jaw 16 is stationary and the other jaw 14 moves toward jaw 16, guided by guide posts 18, 20. The flattened blank 13 is next operated on by upper and lower presser jaws 22, 24 as is illustrated in FIG. 2b. These jaws are L-shaped, with the longer legs 23, 25 of the L being parallel to each other and the shorter legs 26, 27 of each jaw being in slideable contact with the longer leg of the other jaw. The shorter legs have facing work surfaces 28, 30 which, when moved into proximate relationship with each other, define a cylindrical compression zone 32. The flattened tampon blank 13 is placed between the facing work surfaces 28, 30 and these surfaces are then moved into proximate relationship, compressing the blank 13 into the generally cylindrical, radially compressed blank 15.

It will be understood that while the method of radial compression set out above is generally preferred, this is by no means the only possible method for carrying out the prescribed radial compression of this invention. Another suitable method, for example, is described in U.S. Pat. No. 2,798,260 issued to F. Niepmann, et al, on July 9, 1957 and U.S. Pat. No. 3,422,496 issued to K. Wolff, et al, on Jan. 2, 1969. In accordance with these patents, a rolled blank such as blank 12 is centered between two sets of sequentially operated compression jaws members, all acting on the longitudinal sides of the blank to compress the blank radially. The first set is activated to first compress the blank into a form having a cross-like radial cross-section and the second set is then activated to compress the now cross-like blank into a generally cylindrical form.

Figure 3A:
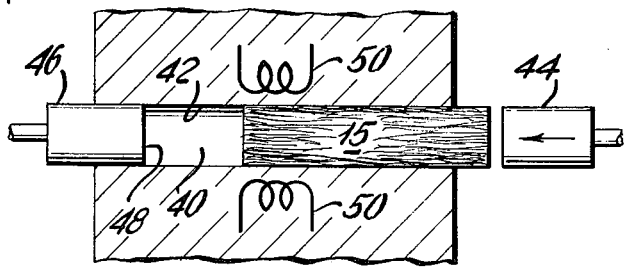
FIGS. 3a–3e schematically illustrate, in longitudinal cross-sectional view, the steps of the method of this invention, carried out in connection with a heated chamber and in particular.

Irrespective of the method for radially compressing the tampon blank, the radially compressed blank, now having a density which may vary from about 0.2 to about 0.5 gm/cc, is next introduced into a compression chamber, as is illustrated schematically in FIG. 3a. Referring to this figure, the radially compressed blank 15 is injected into cylindrical chamber 40 which chamber is defined by walls 42. The blank 15 may be so urged from the radial compression work station (now shown) into chamber 40 by means of a reciprocating pusher 44, which injects the blank into the chamber until it reaches the end of the chamber which, in the embodiment illustrated, corresponds to the face 48 of reciprocating compression piston 46. The walls 42 of chamber 40 are heated, for example, by heating resistors illustrate schematically in FIGS. 3a-e by resistor coils 50. The heating of walls 42 is controlled throughout the entire compression cycle in a manner such that these walls are maintained at a substantially constant temperature which may be selected to range from about 120° to 150° C.

Figure 3B:
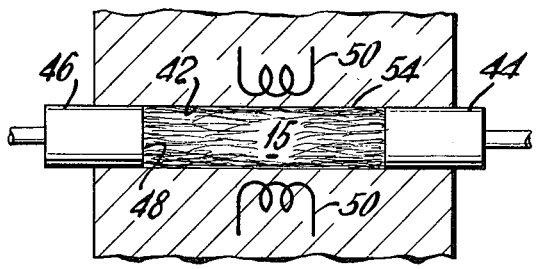

Referring to FIG. 3b, after the blank 5 is completely within the confines of walls 42 of chamber 40, the chamber is closed, this being effected in the specific embodiment by having the pusher 44 and the piston 46 remain at least partially within the chamber to thereby close the openings. It is preferred that throughout the compression cycle, the chamber be maintained in this closed state and thereby retard the loss of ambient moisture generally present and absorbed by the starting fibers. This moisture, the presence of which is highly desirable in the compressing operation, would have a tendency, under the influence of the heating, to desorb from the blank and leave the chamber were it not for the fact that the chamber was closed. While the chamber is illustrated as being closed during this injection step and the subsequent preheating step by means of compression piston 46 and pusher 44, it will be appreciated by those skilled in the art that this is not the only way to close the chamber and, for example, separate closing means may be provided.

Preferably, after the blank has been fully injected into the chamber and the chamber has been closed, the blank is allowed to preheat or equilibrate with the wall temperature for a short period of time, e.g., at least about 5 seconds. While this equilibration period is not essential, it has been found to greatly advance the objective of compressing the blank into a dimensionally stable tampon.

As described above, the blank throughout the steps of radial compression, insertion into the chamber, and preheating is longer than the desired length of the finished tampon and is approximately the same diameter. Preferably, the blank is about 20 to about 40% longer than the desired finished length, and is maintained so throughout the processing steps described thus far, with the exception of a negligible amount of axial compression inherent in the injection step as a result of the axial forces imposed upon the blank by the pusher 44.

Figure 3C:
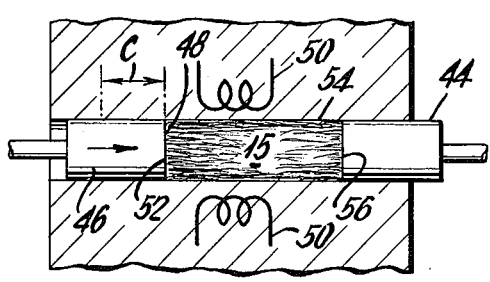

Referring now to FIG. 3c, the preheated blank is now axially compressed by continuously applying a force against its end 52, through a distant indicated in the drawing by the dimension C, while the sides 54 and the other end 56 are held confined within the heated chamber 40. In accordance with this invention, the force is applied to compress the blank to a length equal to less than the desired length of the finished tampon and specifically, the blank is compressed to a length of about 90 to about 98% of the final desired length. It is highly desirable to apply the force as gradually and as uniformly as possible throughout this compression step. For example, it is preferred that no more than 50% of the entire compression of the blank be accomplished in the first 10% of the time interval devoted to this step. Preferably less than 20% of the compression is achieved in the first 10% time increment. While the desire to maximize production rate would indicate that this overcompression step should be carried out as rapidly as possible, it is preferable, from the point of view of product quality, to perform the compression gradually as prescribed above and over a time interval of not less than 1 second and preferably not less than 2 seconds.

Figure 3D:
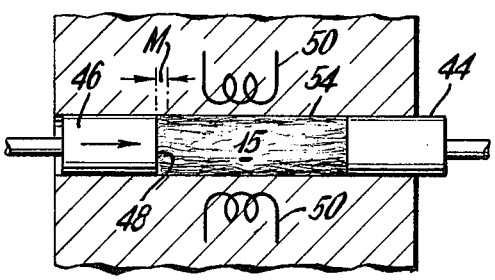

Referring now to FIG. 3d, illustrated therein is the expansion and restraining step in the process of this invention. Upon the tampon blank having been over-compressed to the length prescribed above, the compression force is released to the extent necessary for the blank to expand in length. This expansion is permitted to the extent that the tampon expands to essentially the length desired for the final product. As shown in the drawings, this expansion is accomplished by moving the piston 46 in a direction away from the tampon through a distance indicated by the dimension M. The distance M corresponds to the extent of over-compression, i.e., the difference between the length of the tampon after the over-compression step shown in FIG. 3c and the desired length. It is important that immediately upon the tampon blank reaching this expanded state, sufficient force is now applied to preclude a further expansion. In the illustrated embodiment, this is accomplished by simply maintaining the piston 46 in the position shown in FIG. 3d with the tampon held within the confines of chamber 40. It is important that the tampon be held in the heated chamber in this position for a period of time while still maintaining a force resistant to further expansion. The tampon should be so held for a period of at least 10 seconds and preferably for at least 15 seconds.

Figure 3E:
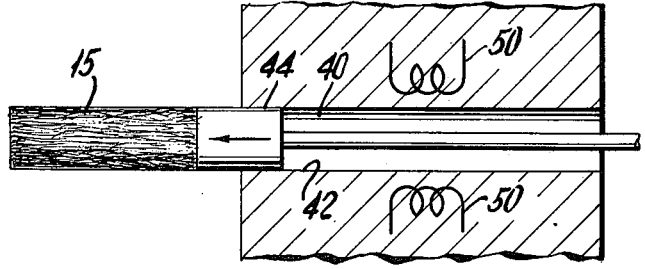

As is illustrated in FIG. 3e, the final step after the above prescribed duration, is to eject the finished, dimensionally stabilized product from the chamber. As shown in FIG. 3e, this is accomplished by withdrawing the piston 46 and ejecting the tampon with pusher 44.

EXAMPLE

A rectangular pad, 250 mm. long, 52 mm. wide, 3 mm. thick and consisting of 70% by weight of 3 denier rayon fibers having an average staple length of 30.2 mm. and 30% by weight of cotton comber fibers having an average length of 9 to 13 mm. is rolled into a cylindrical starting blank, as shown in FIG. 1. The blank is 52 mm. long and has a diameter of 29 mm. The density of the starting blank is 0.0757 gm./cc. The blank is then compressed, in accordance with the method described in connection with FIGS. 2a-b, into a radially compressed blank having a length of 55 mm., a diameter of 12.5 mm., and a density of 0.38 gm./cc. The radially compressed blank is introduced into a heated chamber whose walls are maintained at a substantially constant temperature of 140° C. The chamber is closed and the blank is allowed to equilibrate with the wall temperature for 9 seconds. The blank is then compressed gradually over a period of 4 seconds to an over-compressed length of 40 mm. (the desired final length is 42 mm.).

Upon completion of the above compression step, the tampon is allowed to expand to 42 mm. and then held at that length within the heated chamber for 16.5 seconds. Thereafter, the tampon is ejected.

To summarize, the radially compressed blank is 55 mm. or 30.95% in excess of the desired finished length of 42 mm. The blank is compressed to a length of 40 mm. or 95.24% of the desired finished length and then allowed to expand to the finished length.

As a control, a second blank is prepared and radially compressed in a manner identical to that described above. The control is introduced into the heated chamber and compressed to the desired finished length of 42 mm. and then immediately ejected from the chamber.

The two blanks are left under ambient conditions for 10 seconds after ejection and then measured. The control is found to have expanded substantially whereas, the tampon made in accordance with the teachings of the invention is substantially unexpanded. The two tampons are measured again after 2 hours. Again, the control is found to have expanded somewhat further (less than the initial expansion), whereas the tampon made in accordance with this invention remains unexpanded.

What is claimed is:

1. A method for providing a relatively dimensionally stable absorbent body comprising compressed cellulosic fibers, said method comprising the steps of:
   radially compressing a generally cylindrical blank comprising said cellulosic fibers, said radially compressed blank having a length in excess of the desired finished length;
   introducing said blank into a chamber having heated walls;
   axially compressing said blank to a length less than the desired finished length by continuously applying a force against at least one end of the blank while the sides and other end are held confined within said heated chamber;
   releasing said force to the extent necessary for said blank to expand in length to the desired length; and
   immediately upon having the blank expanded to said desired length, continuously maintaining a force resistant to further expansion against said one end of the blank while still maintaining said blank within the confines of said heated chamber until said blank attains the desired dimensional stability.

2. The method of claim 1 wherein said force resistant to further expansion is maintained for a period of at least about 10 seconds.

3. The method of claim 2 wherein said force resistant to further expansion is maintained for a period of at least about 15 seconds.

4. The method of claim 1 wherein said blank is axially compressed to a length of about 92 to about 98% of the desired finished length.

5. The method of claim 4 wherein said compression is accomplished in a period of time of at least 1 second.

6. The method of claim 5 wherein said period of time is at least 2 seconds.

7. The method of claim 5 wherein less than 50% of the total axial compression is accomplished in the first 10% of said period of time.

8. The method of claim 1 wherein said chamber walls are heated to a temperature of about 120° to about 150° C.

9. The method of claim 1 wherein said radially compressed blank has a length of about 20 to about 40% in excess of the desired finished length.

10. The method of claim 1 wherein the radially compressed blank is compressed to a density of about 0.2 to about 0.7 gm./cc.

* * * * *